United States Patent [19]

Brown

[11] Patent Number: 5,800,431
[45] Date of Patent: Sep. 1, 1998

[54] ELECTROSURGICAL TOOL WITH SUCTION AND CAUTERY

[76] Inventor: Robert H. Brown, Suite 4, 2151 McCallum Rd., Abbotsford, Canada, BC V2S 3N9

[21] Appl. No.: 729,169

[22] Filed: Oct. 11, 1996

[51] Int. Cl.$^6$ .................................... A61B 17/39
[52] U.S. Cl. .................. 606/42; 606/45; 606/49; 604/35
[58] Field of Search ................ 606/42, 45, 46, 606/49; 604/35

[56] References Cited

U.S. PATENT DOCUMENTS

| | | | |
|---|---|---|---|
| 2,275,167 | 3/1942 | Bierman | 606/42 |
| 3,494,363 | 2/1970 | Jackson . | |
| 3,801,766 | 4/1974 | Morrison, Jr. | 606/42 |
| 4,872,454 | 10/1989 | DeOliveira et al. . | |
| 4,911,159 | 3/1990 | Johnson et al. . | |
| 5,071,418 | 12/1991 | Rosenbaum . | |
| 5,160,334 | 11/1992 | Billings et al. | 604/35 |
| 5,318,565 | 6/1994 | Kuriloff et al. . | |
| 5,468,240 | 11/1995 | Gentelia et al. . | |
| 5,620,441 | 4/1997 | Greff et al. | 604/35 |
| 5,674,219 | 10/1997 | Monson et al. | 604/35 |

*Primary Examiner*—Lee S. Cohen
*Attorney, Agent, or Firm*—Fulwider Patton Lee & Utecht, LLP

[57] ABSTRACT

An electrosurgical tool for use with a power source and a suction source includes a handle for gripping by the user and an electrically heatable tip extending from the handle that is selectively electrically connectable to the power source. A suction passage is formed in the handle and is connectable to the suction source. A manually actuatable switch on the body is movable between a default position in which the tip is not electrically connected to the power source and the suction passage is blocked, a cutting position in which the tip is electrically connected to the power source and heated to perform cutting and a coagulating position in which the tip is electrically connected to the power source and heated to perform coagulation. Movement of the switch to each of the cutting and coagulating positions automatically communicates the suction passage with the suction source. The device of the present invention permits electrical cautery (cutting or coagulation) and suction to occur with a single motion of the switch thereby simplifying operation and manipulation of the tool by a surgeon.

9 Claims, 3 Drawing Sheets

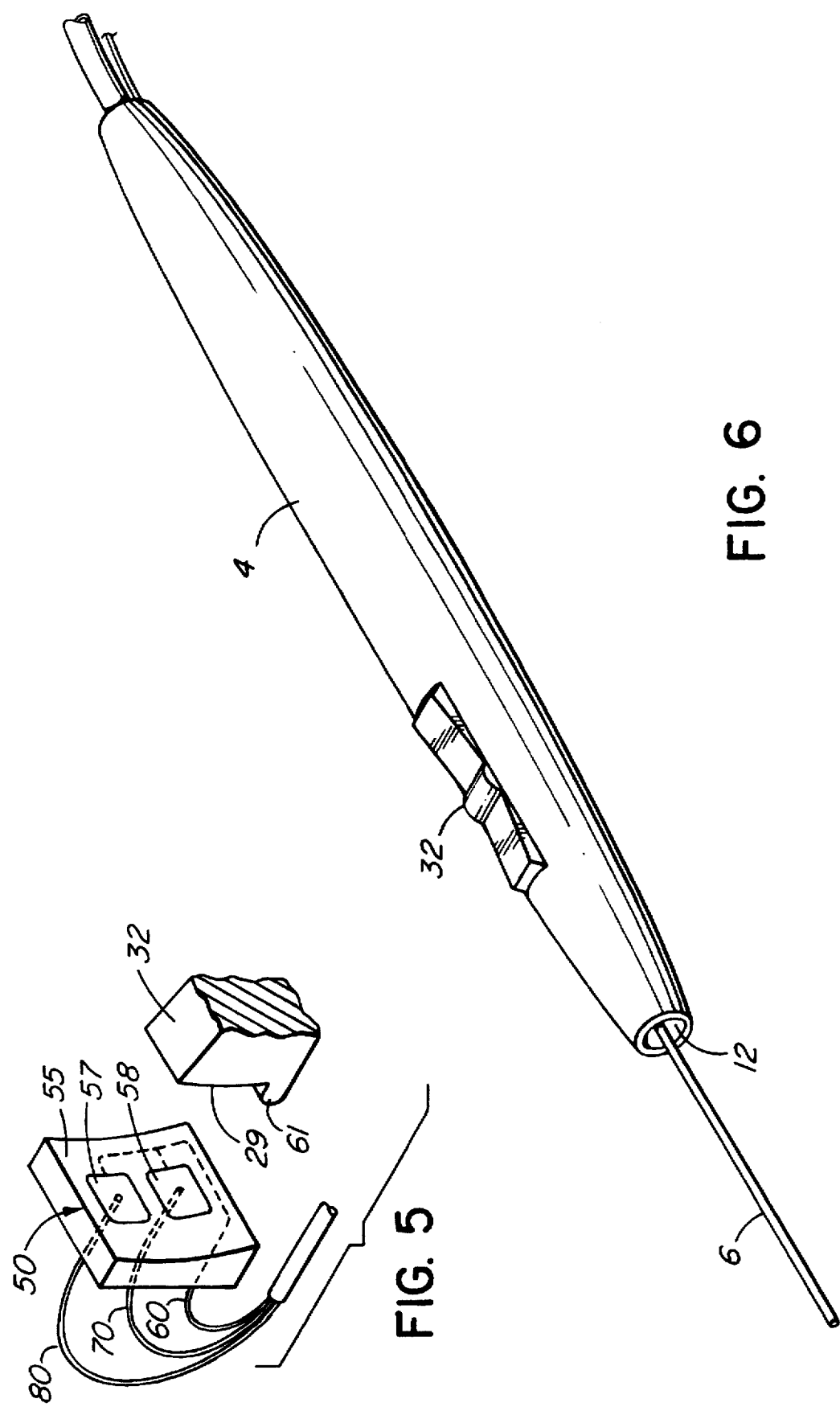

ELECTROSURGICAL TOOL WITH SUCTION AND CAUTERY

FIELD OF THE INVENTION

This invention relates to a medical device, and more specifically, to an electrosurgical tool for performing cutting, suctioning and coagulation of tissue at the operation site.

BACKGROUND OF THE INVENTION

In surgery performed on patients, surgeons generally employ electrosurgical tools to cut tissue and to coagulate bleeding blood vessels in a process known as cautery. An example of a prior art electrosurgical tool is found in U.S. Pat. No. 4,872,454 to DeOliveira et al.

In order to keep the operation site visible, continuous suction devices are used to suction away blood and other debris before they accumulate and to remove smoke that is generated by the electrical cautery process. This suction is vital so that the surgeon's view of the operation site remains unobscured and the operation can proceed safely.

Previously, separate tools were necessary to perform the cautery process and suctioning. If a surgeon uses both tools simultaneously, both hands are occupied which tends to increase the difficulty of the procedure. Use of a separate suctioning device also makes precise positioning of the electrosurgical tool more difficult. To effectively use both devices simultaneously, it is often necessary for an assistant to operate the suction device as the surgeon operates the electrosurgical tool.

To address the foregoing shortcomings of using separate electrosurgical tools and suctioning tools, various combined tools have been developed as disclosed in the following patents:

U.S. Pat. No. 3,494,363 to Jackson
U.S. Pat. No. 4,911,159 to Johnson et al.
U.S. Pat. No. 5,071,418 to Rosenbaum
U.S. Pat. No. 5,318,565 to Kuriloff et al.
U.S. Pat. No. 5,468,240 to Gentelia et al.

The tools disclosed in the above patents use different control schemes for controlling suction while simultaneously operating the cutting and coagulation parts of the tool. In several of the patents, suction must operate continuously as the suction force is also used to control whether the cutting or coagulation function of the tool is selected. This is achieved by the covering or uncovering of various open ports on the body of the tool by the fingers of the user to select a cutting or coagulation mode.

SUMMARY OF THE INVENTION

The present invention provides an electrosurgical tool that combines suction, cutting and coagulation functions. Selection of one of the cutting and coagulation functions by a manually actuatable switch automatically starts operation of the suction action. When the cutting or coagulation functions are not being used, the suction action is automatically stopped.

Accordingly, the present invention provides an electrosurgical tool for use with a power source and a suction source comprising:

a handle for gripping by the user;

an electrically heatable tip extending from the housing and being electrically connectable to the power source;

a suction passage formed in the housing connectable to the suction source; and a manually actuatable switch on the body movable between a default position in which the tip is not electrically connected to the power source and the suction passage is blocked, a cutting position in which the tip is electrically connected to the power source and heated to perform cutting and a coagulating position in which the tip is electrically connected to the power source and heated to perform coagulation, movement of the switch to each of the cutting and coagulating positions automatically communicating the suction passage with the suction source.

Operation of the suction tends to be noisy and employing automatic suction only when the tool is performing cutting or coagulation diminishes irritating and unnecessary noise in the operation room.

BRIEF DESCRIPTION OF THE DRAWINGS

Aspects of the present invention are illustrated, merely by way of example, in the accompanying drawings in which:

FIG. 5 is an exploded view showing details of the switch and the electrical contacts that the switch engages to control cutting and coagulation operations; and FIG. 6 is an isometric view of the surgical tool of the present invention.

DESCRIPTION OF THE PREFERRED EMBODIMENT

Figure 2:
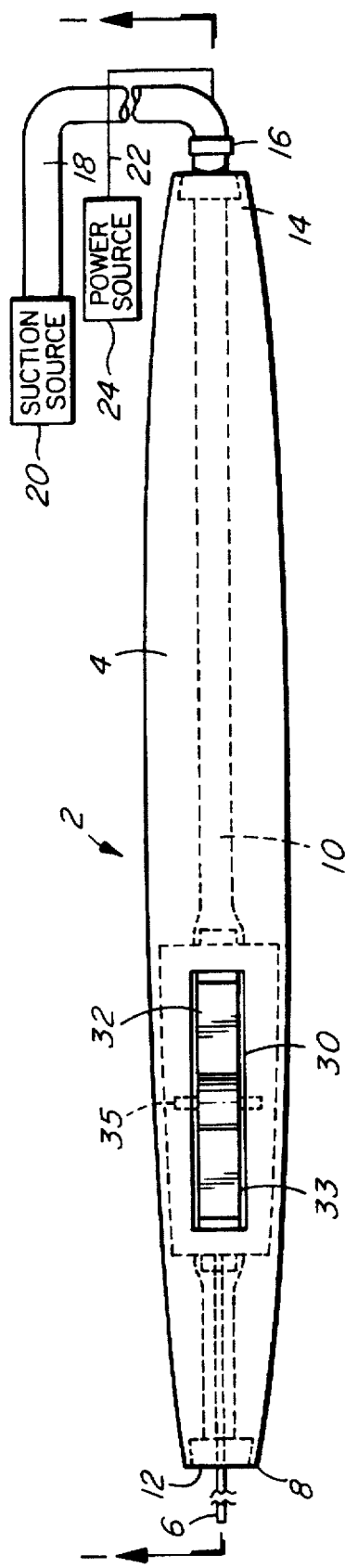
FIG. 2 is a plan view of the electrosurgical tool of FIG. 1.
Figure 1:
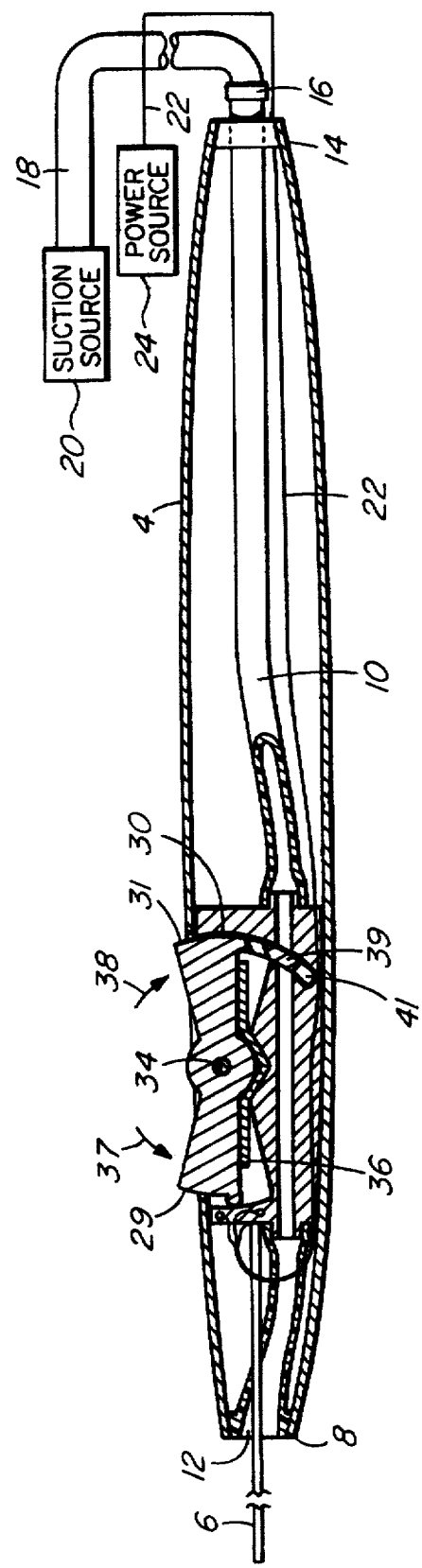
FIG. 1 is a side elevation view with cut away sections taken along line 1—1 of FIG. 2 showing an electrosurgical tool according to a preferred embodiment of the present invention.

Referring to FIGS. 1, 2 and 6, there is shown an electrosurgical tool 2 according to a preferred embodiment of the present invention comprising a moulded handle 4 for comfortable gripping by the user having an electrically heatable tip 6 extending from the front end 8 of the handle. Handle 4 is formed with an internal passage 10 that extends from opening or suction port 12 at front end 8 to a connector 16 at the rear 14 of the handle.

As shown schematically in FIG. 1 and 2, connector 16 is connectable via tubing 18 to a conventional medical suction source 20. Likewise, electrically heatable tip 6 is connected via wiring 22 to a conventional power source 24 that provides current for heating tip 6 to permit cutting or coagulation. Power source 24 is preferably a conventional uni-polar cautery machine. As will be understood by a person skilled in the art, the cautery machine supplies current continuously to tip 6 to allow the attached electrosurgical tool to operate in cutting mode. Tip 6 heats the tissue so that the cells are dessicated very quickly and literally explode to create an incision. In the coagulation mode of the tool, current is delivered in short pulses with pauses between pulses. This results in the tip heating the tissue more slowly resulting in relatively slow dehydration of the cells without exploding.

Heatable tip 6 comprises a rigid metal probe mounted to handle 4 to extend from suction port 12. By appropriate heating of tip 6 as will be discussed further, tip 6 can be used as a cutting instrument or as a tool to coagulate blood vessels.

Intermediate the ends of handle 4, cavity 30 is formed to receive a manually actuatable switch 32 that is used to control the tool of the present invention. Switch 32 simultaneously controls communication of passage 10 with suction source 20 and electrical connection of tip 6 to power source 24. In the preferred embodiment, switch 32 is a rocker switch that pivots about axis 34. The pivotal axis 34 of the switch is preferably defined by a pair of protrusions 35 extending outwardly from sides 33 of the switch adapted for a snap fit into corresponding openings formed in the side walls of cavity 30. The end walls of cavity 30 are curved to accommodate the front and rear curved end walls 29 and 31, respectively, of switch 32.

Figure 3:
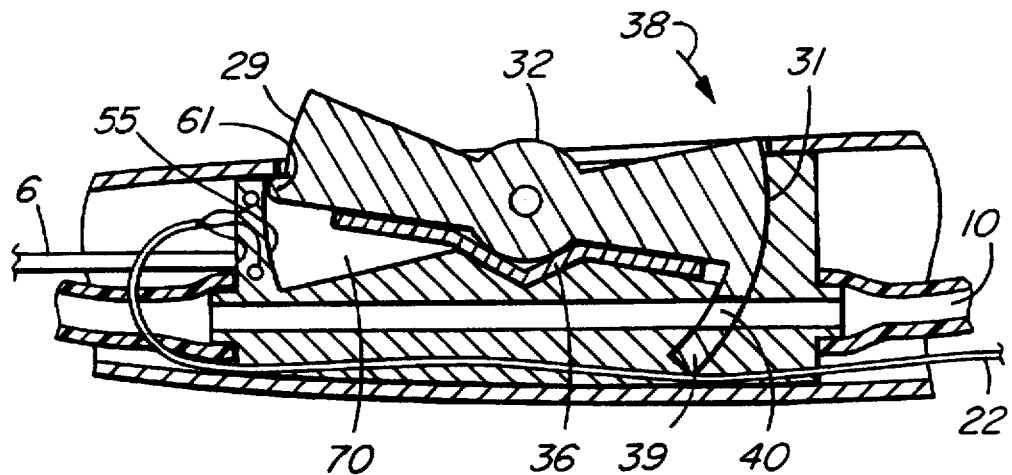
FIG. 3 is a detail view of the manually actuatable switch of the tool pivoted to a position in which the tip is heated and the suction passage is open.

Switch 32 rests in a default intermediate position, shown in FIG. 1, in which tip 6 is not electrically connected to power source 24 and the suction passage is not in communication with suction source 20. The default intermediate position of switch 32 is maintained by spring clip 36 having essentially an inverted W shape that is mounted in cavity 30 below switch 32. Switch 32 is pivotable about axis 34 by pressing on opposite sides of the switch (as indicated by arrows 37 and 38). When pivoted in one direction as best shown in FIG. 3, the switch is moved to a cutting position in which tip 6 is electrically connected to the power source so that the tip is heated to perform cutting and suction passage 10 is automatically communicated with suction source 20 to create suction at port 12. When pivoted in the other direction as shown in FIG. 4, the switch is moved to a coagulation position in which tip 6 is electrically connected to the power source so that it is heated to perform coagulation and suction passage 10 is automatically communicated with suction source 20.

Figure 4:
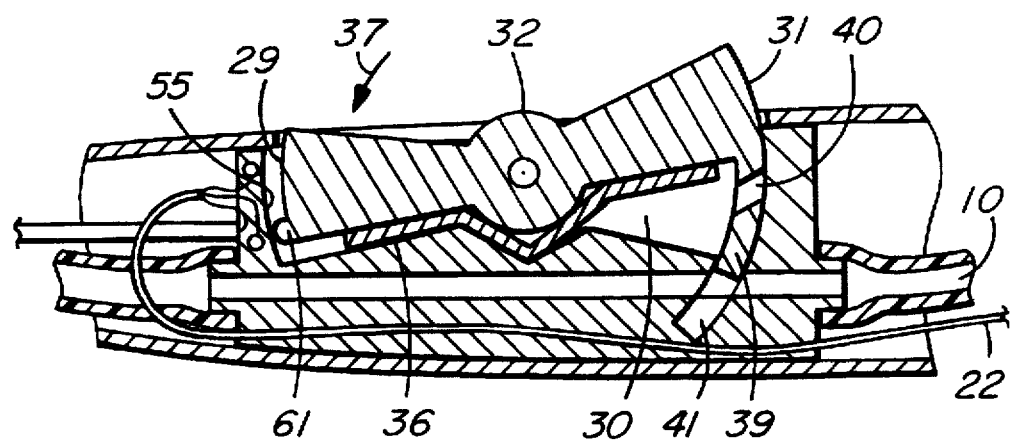
FIG. 4 is a detail view of the switch pivoted in the opposite direction from that shown in FIG. 3.

FIGS. 3 and 4 are detail views of the rocker switch and illustrates the manner in which the switch operates to automatically provide suction on depression of either side of the switch. Rocker switch 32 includes a portion 39 that extends downwardly from the rear wall 31 of the switch. Portion 39 is formed with a port 40 therethrough. As best shown in FIG. 4, handle 4 includes a curvilinear passage 41 that extends downwardly from cavity 30 to intersect suction passage 10.

When switch 32 is installed in cavity 30 in the default position, portion 39 is introduced into passage 41 and extends into and blocks suction passage 10 to prevent communication of suction port 12 with the suction source (see FIG. 1). When switch 32 is pivotable forwardly as indicated by arrow 37 in FIG. 4, portion 39 is raised out of passage 10 to communicate the suction passage with the suction source to establish suction at port 12 adjacent tip 6. As switch 32 is pivoted rearwardly as indicated by arrow 38 in FIG. 3, portion 39 is moved such that port 40 is aligned with passage 10 to establish suction at port 12. Preferably, a seal member is provided at the junction between passages 10 and 41 to permit slidable movement of portion 39 through the seal and limit leakage about portion 39.

At the same time that switch 32 is blocking or unblocking passage 10 at rear wall 31 using portion 39, the front wall 29 of the switch is operating an electrical circuit to electrically connect tip 6 to power source 24 for cutting or coagulation.

FIG. 5 provides details of a preferred electrical circuit 50. Wiring 22 connecting power source 24 to handle 4 extends within handle 4 to the curved front face 55 of cavity 30. At front face 55, wiring 22 separates into three leads 60, 70 and 80. Common lead 60 connects power source 24 to tip 6 and is connected to upper and lower contacts 57 and 58 mounted to front face 55. Upper contact 57 is connected to lead 80 and lower contact 58 is connected to lead 70. Normally, contacts 57 and 58 are open to prevent electrical connection between tip 6 and power source 24. Front wall 29 of rocker switch 32 is formed with a protrusion 61 that is adapted to engage with and close upper contact 57 or lower contact 58 whenever the switch is rocked rearwardly (arrow 38 in FIG. 3) or forwardly (arrow 37 in FIG. 4), respectively, to complete the circuit and energize tip 6 with the current associated with a particular movement of the rocker switch. When switch 32 is in the default position, protrusion 61 rests between the upper and lower contacts.

Lead 70 or lead 80, dependent on which contact is closed, provides current from power source 24 to heat tip 6 in a manner suitable for cutting or coagulation of tissue. For example, if lead 70 is connected to power source 24 to provide continuous current when upper contact 57 is closed, lead 70 provides the cutting function for the tool. If lead 80 is connected to power source 24 to provide pulsed current when lower contact 58 is closed, lead 80 provides the coagulation function for the tool.

Contacts 57 and 58 are illustrated in FIG. 4 as being resilient flaps of electrically conductive material that are pressed by protrusion 61 to complete a circuit with lead 70 or lead 80. It will be readily apparent to a person skilled in the art that contacts 57 and 58 can be formed from any suitable selector switches that are urged from an open state into a closed state by movement of rocker switch 32.

Furthermore, it will be readily apparent that the direction that switch 32 is rocked to select for cutting or coagulation is dependent on whether current for cutting or current for coagulation is being delivered to the upper or lower contact. Rocker switch 32 is preferably marked with an appropriate designation such as CUT and COAG on the surface of the rocker switch that must be depressed to achieve the indicated operation.

Preferably, depending portion 39 and protrusion 61 of switch 32 are positioned and dimensioned such that suction passage 10 is opened to create suction at port 12 just before tip 6 is electrically connected to the power source. This arrangement ensures that the operation site is always initially cleared of blood, fluid or other debris prior to performing further cutting or coagulation. By placing suction port 12 directly at the front of handle 4 adjacent tip 6, any fluid, smoke or debris generated by tip 6 is immediately suctioned away to keep the surgeon's field of view clear.

Although the present invention has been described in some detail by way of example for purposes of clarity and understanding, it will be apparent that certain changes and modifications may be practised within the scope of the appended claims.

I claim:

1. An electrosurgical tool for use with a power source and a suction source comprising:

a handle for gripping by the user;

an electrically heatable tip extending from the handle and being electrically connectable to the power source;

a suction passage formed in the handle connectable to the suction source; and a manually actuatable rocker switch on the body including a portion that extends into and blocks the suction passage to prevent communication with the suction source when the switch is in a default position in which the tip is not electrically connected to the power source, the rocker switch being movable to a cutting position in which the tip is electrically connected to the power source and heated to perform cutting and a coagulating position in which the tip is electrically connected to the power source and heated to perform coagulation, movement of the rocker switch to each of the cutting and coagulating positions automatically communicating the suction passage with the suction source by moving the rocker switch portion to unblock the suction passage.

2. An electrosurgical tool as claimed in claim 1 including a spring to bias the switch to the default position being the intermediate position of the switch between a forwardly pivoted and a rearwardly pivoted position corresponding to one of the cutting and the coagulation positions.

3. An electrosurgical tool as claimed in claim 1 in which the rocker switch portion is formed with at least one opening therethrough that is pivotable into alignment with the suction passage when the rocker switch is pivoted to one of the cutting and the coagulation positions.

4. An electrosurgical tool as claimed in claim 1 including an electrical circuit operable by the rocker switch to electrically connect the tip to the power source.

5. An electrosurgical tool as claimed in claim 4 in which the electrical circuit includes a pair of contacts which are open when the rocker switch is in the default position to disconnect the tip from the power source and which are selectively closed when the rocker switch is moved to the cutting position or the coagulation position to deliver power to the tip to provide cutting or coagulation, respectively.

6. An electrosurgical tool as claimed in claim 5 in which the contacts comprise first and second selector switches that are urged from an open state into a closed state by a protrusion on the rocker switch.

7. An electrosurgical tool as claimed in claim 1 in which the manually actuatable switch is adapted to automatically communicate the suction passage with the suction source before the electrically heatable tip is electrically connected to the power source.

8. An electrosurgical tool as claimed in claim 1 in which the suction passage terminates in a suction port in the handle adjacent the point at which the electrically heatable tip extends from the handle.

9. An electrosurgical tool as claimed in claim 1 in which the electrically heatable tip comprises a rigid metal probe extending from the handle.

* * * * *